United States Patent
Auricchio et al.

(10) Patent No.: US 9,669,223 B2
(45) Date of Patent: Jun. 6, 2017

(54) SYSTEM FOR LEADLESS PACING OF THE HEART

(71) Applicant: SORIN CRM SAS, Clamart (FR)

(72) Inventors: Angelo Auricchio, Ruvigliana (CH); Luca Vitali, Strambino (IT)

(73) Assignee: SORIN CRM SAS, Clamart (FR)

( * ) Notice: Subject to any disclaimer, the term of this patent is extended or adjusted under 35 U.S.C. 154(b) by 382 days.

(21) Appl. No.: 14/188,502

(22) Filed: Feb. 24, 2014

(65) Prior Publication Data
US 2014/0243848 A1    Aug. 28, 2014

(30) Foreign Application Priority Data
Feb. 25, 2013 (EP) .................................... 13156624

(51) Int. Cl.
| | | |
|---|---|---|
| *A61B 19/00* | (2006.01) | |
| *A61N 1/362* | (2006.01) | |
| *A61N 1/372* | (2006.01) | |
| *A61N 1/375* | (2006.01) | |
| *A61N 1/05* | (2006.01) | |

(52) U.S. Cl.
CPC ......... *A61N 1/362* (2013.01); *A61N 1/37205* (2013.01); *A61N 1/37217* (2013.01); *A61N 1/3756* (2013.01); *A61N 2001/0578* (2013.01)

(58) Field of Classification Search
CPC .... A61N 1/362; A61N 1/378; A61N 1/37217; A61N 1/04; A61N 1/05; A61N 2001/0578; A61N 1/18; A61N 1/36; A61N 1/375; A61N 1/3605; A61B 17/3468; A61B 19/00
See application file for complete search history.

(56) References Cited

U.S. PATENT DOCUMENTS

| | | | |
|---|---|---|---|
| 5,036,854 A | | 8/1991 | Schollmeyer et al. |
| 5,156,151 A | * | 10/1992 | Imran .................... A61N 1/056 600/375 |

(Continued)

FOREIGN PATENT DOCUMENTS

| | | |
|---|---|---|
| EP | 2 520 329 | 11/2012 |
| WO | WO-2012/015757 A1 | 2/2012 |

OTHER PUBLICATIONS

Search Report for European Patent Application No. 13156624.2, dated Jun. 6, 2013, 8 pages.

*Primary Examiner* — Victor Nguyen
(74) *Attorney, Agent, or Firm* — Foley & Lardner

(57) ABSTRACT

Devices for use in providing stimulation to cardiac tissue are provided. One device is configured for implantation in or near the heart and includes a flexible, elongate body. The body is configured to be positioned across two different sections of the vasculature such that (a) the first end can be positioned in a first section of the vasculature through which the device can stimulate a first chamber of the heart and (b) the second end can be positioned in a second section of the vasculature through which the device can stimulate a second chamber of the heart. The device further includes a receiver circuit configured to receive signals wirelessly from a transmitter device and to convert the signals into electrical power. The device also includes at least a first set of one or more electrodes configured to stimulate the heart using the electrical power.

17 Claims, 14 Drawing Sheets

(56) References Cited

U.S. PATENT DOCUMENTS

| | | | |
|---|---|---|---|
| 5,766,234 A * | 6/1998 | Chen | A61B 17/00234 600/373 |
| 2006/0095078 A1 | 5/2006 | Tronnes | |
| 2006/0224225 A1 | 10/2006 | Ransbury et al. | |
| 2007/0179552 A1 | 8/2007 | Dennis et al. | |

\* cited by examiner

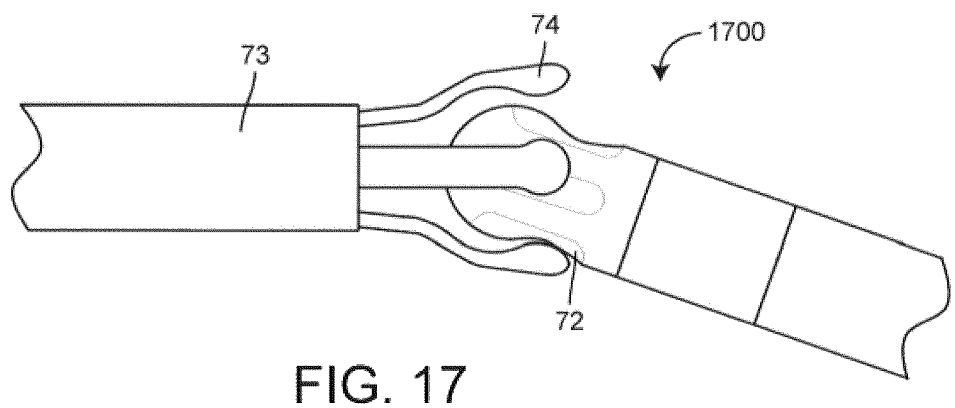
FIG. 17
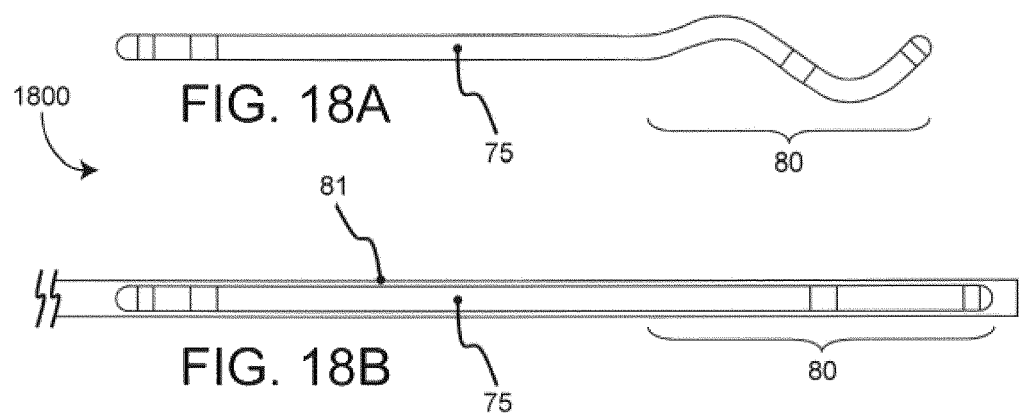
FIG. 18A
FIG. 18B

SYSTEM FOR LEADLESS PACING OF THE HEART

CROSS-REFERENCE TO RELATED PATENT APPLICATIONS

This application claims priority from European Patent Application No. 13156624.2 entitled "System for Leadless Pacing of the Heart" filed on Feb. 25, 2013, which is incorporated herein by reference in its entirety.

BACKGROUND

The present invention relates generally to the field of pacing systems for the heart. More specifically, the present invention relates to implantable devices configured to be implanted in and/or near the heart and provide electrical stimulation to the heart using signals (e.g., power signals) received wirelessly from a transmitter.

Traditionally, pacing of the heart has been performed using electrodes positioned within the human body that are connected to a transmitter (e.g., implanted subcutaneously) using leads extending from the transmitter to the electrodes. Running leads from a location deep inside the body to a location near the skin where the transmitter is implanted is invasive and presents a variety of challenges and risks for the health of the patient. There is a need for a system that allows effective pacing of the heart and is less invasive than traditional pacing systems.

SUMMARY

One embodiment relates to a device that is configured for implantation in a vasculature within or proximate to a heart of a patient so as to accommodate stimulation of at least one of a first chamber and a second chamber of the heart. The device includes a flexible, elongated body that has a first end and an opposite second end, wherein the body has a substantially isodiametric tubular shape across a length of the body between the first end and the opposite second end. The body is configured to be positioned across two different sections of the vasculature such that (a) the first end can be positioned in a first section of the vasculature through which the device can stimulate the first chamber of the heart and (b) the second end can be positioned in a second section of the vasculature through which the device can stimulate the second chamber of the heart. The device further includes a receiver circuit configured to receive signals wirelessly from a transmitter device and to convert the signals into electrical power. The device further includes at least a first set of one or more electrodes that is positioned on the body proximate to the first end and that is configured to receive the electrical power from the receiver circuit and to stimulate the heart.

Another embodiment relates to a deployment device for inserting a wireless stimulation device in vasculature within or proximate to a heart of a patient, the wireless stimulation device having an elongated, flexible body with a substantially isodiametric tubular shape across a length of the body and being configured to stimulate the heart using signals received wirelessly from a transmitter device. The deployment device includes an elongated body having a first end configured to be inserted into the vasculature and a second end configured to extend outside of the patient and be used to control movement of the deployment device. The deployment device further includes a clamping device coupled to the first end of the elongated body and configured to be releasably coupled to an end of the wireless stimulation device. The clamping device may include a plurality of prongs configured to clamp around a proximal end of the wireless stimulation device. At least one of the plurality of prongs is configured to recess at least partially into at least one indentation of the proximal end of the wireless stimulation device and to allow the deployment device to rotate the wireless stimulation device. The clamping device is configured to be disengaged and reengaged from the wireless stimulation device within the vasculature without requiring removal of the clamping device and wireless stimulation device from the patient. The clamping device is further configured to attach the elongate body of the deployment device to the body of the wireless stimulation device in a substantially coaxial configuration, such that a user of the deployment device may push the wireless stimulation device ahead of the clamping device and pull the wireless stimulation device behind the clamping device through the vasculature during implantation of the wireless stimulation device.

Another embodiment relates to a wireless stimulation device that is configured for implantation in a vasculature within or proximate to the heart of a patient so as to accommodate stimulation of at least one of a first chamber and a second chamber of the heart. The device includes a flexible, elongated body that has a first end and an opposite second end, wherein the body is configured to be positioned across two different sections of the vasculature such that (a) the first end can be positioned in the first section of the vasculature through which the device can stimulate a first chamber of the heart and (b) the second end can be positioned in the second section of the vasculature through which the device can stimulate a second chamber of the heart. The device further includes a receiver circuit configured to receive signals wirelessly from a transmitter device and to convert the signals into electrical power. The device further includes at least a first set of one or more electrodes that is positioned on the body proximate to the first end and that is configured to receive the electrical power from the stimulation circuit and to stimulate the heart. The body comprises a deployment attachment on at least one of the first end and second end configured to couple releasably to a plurality of prongs of a deployment device that is configured to insert the wireless stimulation device into the vasculature. The deployment attachment (a) includes one or more indentations into which one or more prongs are configured to recess to allow the deployment device to rotate the wireless stimulation device and (b) is configured to allow the deployment device to disengage and reengage from the wireless stimulation device within the vasculature without requiring removal of the deployment device and wireless stimulation device from the patient.

In some implementations of the exemplary embodiments described above, the receiver circuit is configured to receive the signals wirelessly from the transmitter device, to convert the signals into electrical power, and to transmit the electrical power directly to the one or more electrodes to stimulate the heart.

In some implementations of the exemplary embodiments described above, a wireless stimulation device further includes (A) an energy storage device configured to receive and to store the electrical power from the receiver circuit and (B) a stimulation circuit configured to transmit stimulation signals to the one or more electrodes using the electrical power stored in the energy storage device. In some embodiments, the signals received from the transmitter include control signals configured to control one or more parameters of the stimulation signals transmitted to the one or more electrodes by the stimulation circuit. In some embodiments, the stimulation circuit includes a stimulation control circuit configured to control the provision of stimulation to the heart by the one or more electrodes without requiring external control signals to be received from the transmitter device.

In some implementations of the exemplary embodiments described above, a wireless stimulation device further includes a second set of one or more electrodes positioned on the body proximate to the second end and configured to receive the electrical power from the receiver circuit and to stimulate the heart. In some embodiments, the first set of electrodes is positioned within the first section of the vasculature and the second set of electrodes is positioned within the second section of the vasculature, at least one of the first section and the second section of the vasculature into which the body is configured to be positioned is external to the heart, and at least one of the first set of electrodes and the second set of electrodes is configured to stimulate epicardially at least one of the first chamber and the second chamber of the heart. In some embodiments, the first section of the vasculature includes a coronary vein and the second section of the vasculature includes a coronary sinus, the first set of electrodes is configured to stimulate epicardially a left ventricle of the heart, and the second set of electrodes is configured to stimulate epicardially a left atrium of the heart.

In some implementations of the exemplary embodiments described above, the first and second ends are open ends and wherein the body has a central lumen that communicates with both ends. In some implementations, the first and second ends are closed ends.

In some implementations of the exemplary embodiments described above, the receiver circuit includes a plurality of coils distributed across a length of the body.

In some implementations of the exemplary embodiments described above, the receiver circuit is configured to receive the signals from the transmitter device using one or more of inductive coupling, radio frequency radiation, and ultrasound radiation. In some embodiments, the receiver circuit is configured to receive power signals from the transmitter device using one of inductive coupling, radio frequency radiation, and ultrasound radiation, and the receiver circuit is configured to receive control signals configured to control one or more parameters of stimulation provided to the heart using another of inductive coupling, radio frequency radiation, and ultrasound radiation.

In some implementations of the exemplary embodiments described above, at least one of the first end and the second end of the body comprises a deployment attachment configured to allow a deployment device to disengage and reengage from the body within the vasculature without requiring removal of the deployment device and body from a patient.

In some implementations of the exemplary embodiments described above, at least one of the first end and the second end of the body comprises an anchoring attachment configured to stabilize at least a portion of the device in a substantially immobile position after the device has been inserted in the vasculature. In some embodiments, the anchoring attachment and at least one of the one or more electrodes together comprise an active stent.

In some implementations of the exemplary embodiments described above, the device is configured for use during a magnetic resonance imaging (MRI) procedure.

In some implementations of the exemplary embodiments described above, the device further includes an energy harvesting circuit configured to generate electrical energy to be used in stimulating the heart from flexural motion generated during a cardiac cycle.

In some implementations of the exemplary embodiments described above, a deployment device further includes a sleeve configured to slide longitudinally along the elongated body, and the sleeve is configured to slide forward to cause the prongs to engage the wireless stimulation device and slide backward to cause the prongs to disengage from the wireless stimulation device.

In some implementations of the exemplary embodiments described above, a deployment device is configured to position the wireless stimulation device in a position for the wireless stimulation device to stimulate epicardially at least one chamber of the heart.

In some implementations of the exemplary embodiments described above, a deployment device comprises a central lumen, and wherein the wireless stimulation device is deployed through the use of a guiding wire.

BRIEF DESCRIPTION OF THE DRAWINGS

The disclosure will become more fully understood from the following detailed description, taken in conjunction with the accompanying figures, wherein like reference numerals refer to like elements, in which:

FIG. 17 is an illustration of the deployment system of FIG. 13 demonstrating engagement of the deployment device with the deployment attachment of the wireless stimulation device when the deployment device and deployment attachment are slightly misaligned according to an exemplary embodiment;

FIG. 18A is an illustration of a wireless stimulation device having a bent portion configured to anchor the wireless stimulation device in place in the vasculature according to an exemplary embodiment;

FIG. 18B is an illustration of the wireless stimulation device of FIG. 18A in which the wireless stimulation device, including the bent anchoring portion, is held substantially straight within a deployment catheter according to an exemplary embodiment;

DETAILED DESCRIPTION

The figures illustrate exemplary embodiments, but it should be understood that the application is not limited to the details or methodology set forth in the description or illustrated in the figures. It also should be understood that the terminology is for the purpose of description only and should not be regarded as limiting. As discussed below, the systems and methods can be utilized in a number of control devices for various types of applications or analyzed systems.

With reference to the figures generally, systems and methods are shown, according to various exemplary embodiments, for delivering electrical stimuli to the heart by the use of an implantable wireless stimulation device. The wireless stimulation device has an elongated, flexible body (e.g., a tubular or "worm-like" body) intended to be implanted within the vasculature in or near the heart. In some embodiments, the body has sufficient length such that it is configured to be positioned across two different sections of the vasculature through which two different chambers of the heart may be stimulated. In some embodiments, at least a portion of the body may be positioned outside of the heart, and the wireless stimulation device may be used to stimulate epicardially at least one chamber of the heart. The wireless stimulation device includes at least one set of one or more electrodes positioned on the body proximate to at least one end of the body. In some embodiments, the wireless stimulation device includes a set of one or more electrodes positioned proximate to each end of the wireless stimulation device. The electrodes are configured to provide electrical stimulation to one or more chambers of the heart. The wireless stimulation device includes a receiver circuit that is configured to wirelessly receive signals from a transmitter device and convert the signals into electrical power that may be used to provide stimulation via the electrodes. In some embodiments, signals received from the transmitter device may also include control signals used to configure one or more parameters (e.g., timing, amplitude, etc.) of the stimulation provided by the wireless stimulation device. In some embodiments, the wireless stimulation device includes control circuitry (e.g., as part of a stimulation circuit) configured to implement switching and/or timing functions to implement a desired pacing scheme. In various embodiments, various devices and methods may be used to deploy the wireless stimulation device into the body and/or attach the wireless stimulation device into position once the wireless stimulation device has reached the desired implant site.

Figure 1:
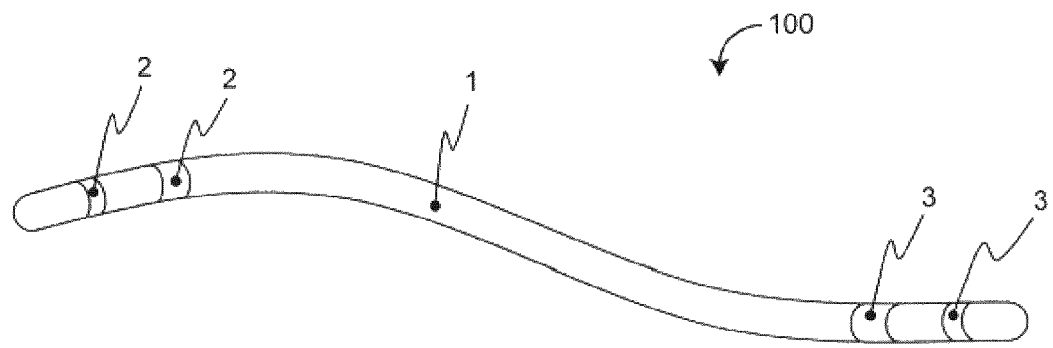
FIG. 1 is an illustration of a wireless stimulation device according to an exemplary embodiment.

With reference to FIG. 1, an illustration of a wireless stimulation device 100 used to stimulate the heart is shown, according to an illustrative embodiment. Device 100 is configured to be implanted within the vasculature of a patient in or near the patient's heart. The term "vasculature," as used herein, should be understood to include both blood vessels (e.g., veins) near the heart as well as portions (e.g., cavities or chambers) of the heart itself. Device 100 is a receiver device that is configured to receive signals wirelessly from a transmitter device, convert the signals into electrical power, and use the electrical power to stimulate the heart. Device 100 may also be configured to sense or measure parameters related to the cardiac cycle, such as measuring capture of stimuli provided by the electrodes.

Wireless stimulation device 100 includes an elongated, flexible body 1 having a first pair of electrodes 2 proximate to a first end of device 100 and a second pair of electrodes 3 proximate to a second end of device 100. Device 100 is configured to be placed in the heart chronically and to provide stimulation to at least one chamber of the heart via electrode 2 and/or electrode 3.

Body 1 may have a substantially tubular or cylindrical shape with, for instance, a circular (e.g., elliptical) or rectangular cross-section. Body 1 may be constructed from any material that is flexible enough to allow body 1 to be maneuvered through the vasculature of the human body (e.g., via venous access), including through curves in the vasculature. Illustrative of such materials are silicone, polyurethane (e.g., Pellethane® 2363), co-polymers such as silicone-polyurethane, ethylene tetrafluoroethylene (ETFE), and polytetrafluoroethylene (PTFE), e.g., Teflon®, among other types of materials.

In some embodiments, body 1 may have a length that is at least an order of magnitude larger than its width. In various embodiments, the length of body 1 may be greater than approximately 2 cm, up to approximately 10 cm, up to approximately 20 cm, greater than approximately 20 cm, etc. In some embodiments, a longer length may be utilized for body 1 to provide more efficient energy transfer from a transmitter device and/or allow for greater generation of electrical energy by an energy harvesting circuit, as will be described in greater detail below.

In some embodiments, electrode 2 and/or electrode 3 may be cylindrical and may be designed to be substantially flush with an outer circumference of body 1; i.e., such that body 1 and electrodes 2 and/or 3 have substantially the same radial diameter. In other embodiments, electrode 2 and/or electrode 3 may be configured to extend further out radially than an outer surface of body 1. In still further embodiments, electrodes 2 and/or 3 may be connected to body 1 and have a non-cylindrical shape (e.g., a spherical shape). All variations of electrode placement and/or geometry are contemplated within the present disclosure.

With reference to FIGS. 2 through 6, illustrations are provided according to exemplary embodiments that show various positions, among others, in which a wireless stimulation device may be placed in the vasculature in or near the heart. In some embodiments, the wireless stimulation device may be positioned in a manner such that the body of the device spans across multiple sections of the vasculature. For instance, a first end of the device may be positioned in a first section of the vasculature through which the device can stimulate a first chamber of the heart, and a second end of the device may be positioned in a second section of the vasculature through which the device can stimulate a second chamber of the heart. In some embodiments, the device may span more than two sections of the vasculature and/or may include more than two sets of electrodes configured to stimulate different chambers of the heart.

In some embodiments, one or more portions of the body may be positioned in a portion of the vasculature external to the heart and may have electrodes positioned proximate to the external portions configured to stimulate epicardially one or more chambers of the heart. In endocardial placement of an electrode, the size, location, and movement of the receiver may result in an inefficient, unreliable, and possibly discontinuous transfer of transmitted energy. Exemplary embodiments of the present disclosure may overcome these obstacles. Inefficient transmission leads to greater battery power requirements to power the device and/or premature depletion of batteries. In endocardial pacing, the receiver antenna may need to be placed close to the transmitter when the antenna is small, or if the antenna is larger, it may be placed remotely. A small stimulation device/antenna requires greater precision in staying within the emitted field than larger antennas. A small change in body position may expose the stimulation device to great changes in orientation with respect to the field, resulting in increased inefficiency of energy transfer. Larger receivers may experience problems with fixation (stable mechanical anchoring), local necrosis, and/or greater risk of systemic thrombosis due to incomplete endothelialization process. In some embodiments, one or more portions of the stimulation device of the present invention may be configured for placement epicardially, e.g., in the coronary sinus and coronary vein, and thus may overcome one or more of these limitations.

Figure 2:
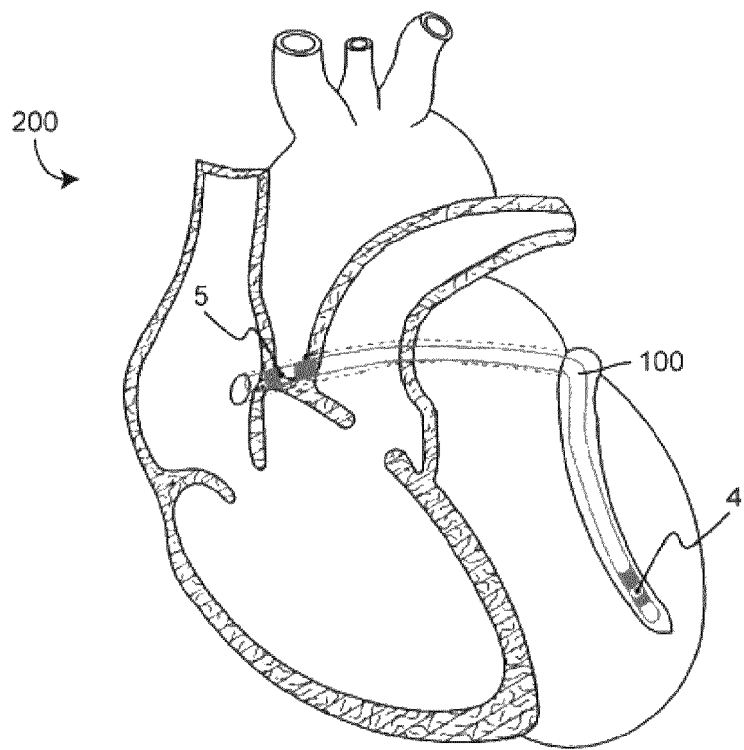
FIG. 2 is an illustration of a first example positioning of the wireless stimulation device of FIG. 1 within a human body according to an exemplary embodiment.

With reference to FIG. 2, a first example position 200 of device 100 within a human body is shown. In position 200, a first end 4 of device 100 is located in a coronary vein, and from that position electrodes proximate to end 4 may be configured to epicardially pace the left ventricle (LV). A second end 5 of device 100 is located in the coronary sinus, in which position electrodes proximate to end 5 may be configured to pace the left atrium (LA). In this configuration, pacing schemes configured to pace the heart by stimulating the LV and LA may be utilized, such as sequential LA-LV pacing schemes.

Figure 3:
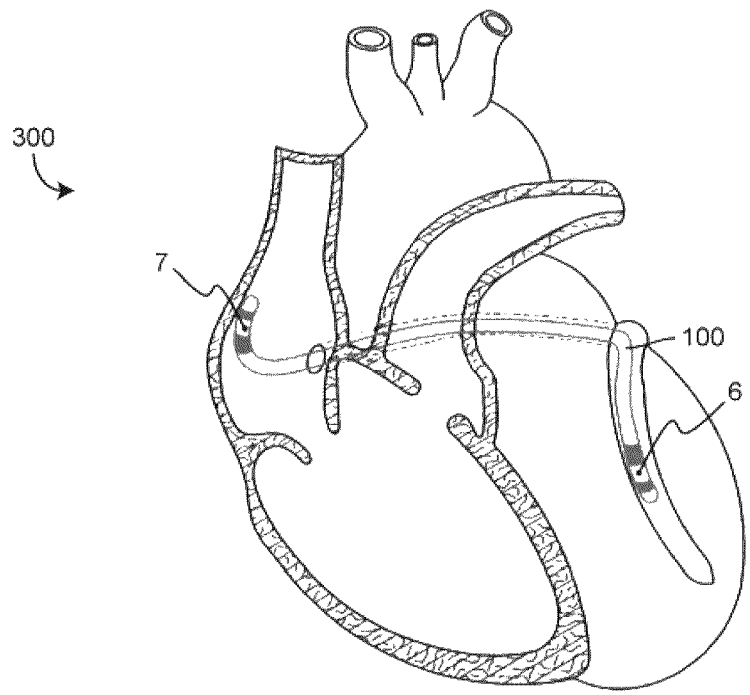
FIG. 3 is an illustration of a second example positioning of the wireless stimulation device of FIG. 1 within a human body according to an exemplary embodiment.

FIG. 3 illustrates a second example position 300 of device 100 within the vasculature in or near the heart. In position 300, a first end 6 of device 100 is located in a coronary vein and a second end 7 is positioned in a location appropriate for pacing the right atrium (RA), such as on the RA wall or in another position in or near the RA. Position 300 may be used to carry out a pacing scheme involving stimulation of the RA and LV, such as a sequential RA-LV pacing scheme.

Figure 4:
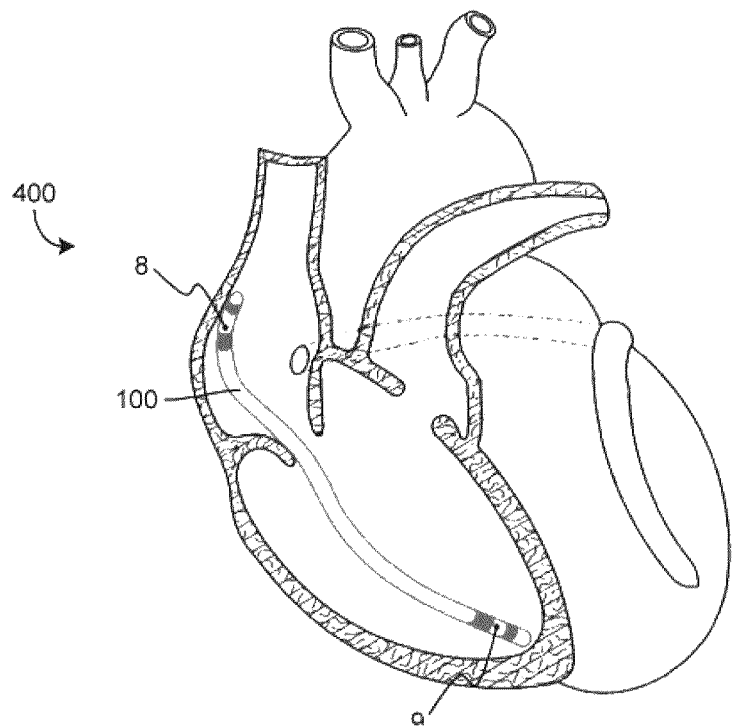
FIG. 4 is an illustration of a third example positioning of the wireless stimulation device of FIG. 1 within a human body according to an exemplary embodiment.

FIG. 4 illustrates a third example position 400 of device 100 within the vasculature in or near the heart. In position 400, a first end 8 is located in a position appropriate for pacing the RA, and a second end 9 is positioned in the right ventricular (RV) apex. Position 400 may be used to carry out a pacing scheme involving stimulation of the RA and RV, such as a sequential RA-RV pacing scheme.

In various embodiments, placement of the ends of device 100 may be made in various other positions of the vasculature that allow pacing of the various chambers of the heart. For example, pacing of the RV is accomplished in position 400 by placing second end 9 of device 100 in the RV apex, but second end 9 could alternatively be positioned on the interventricular septum, in the right ventricular outflow tract (RVOT), or in any other location sufficient to allow stimulation of the RV. All such variations in positioning are contemplated within the present disclosure.

Figure 5:
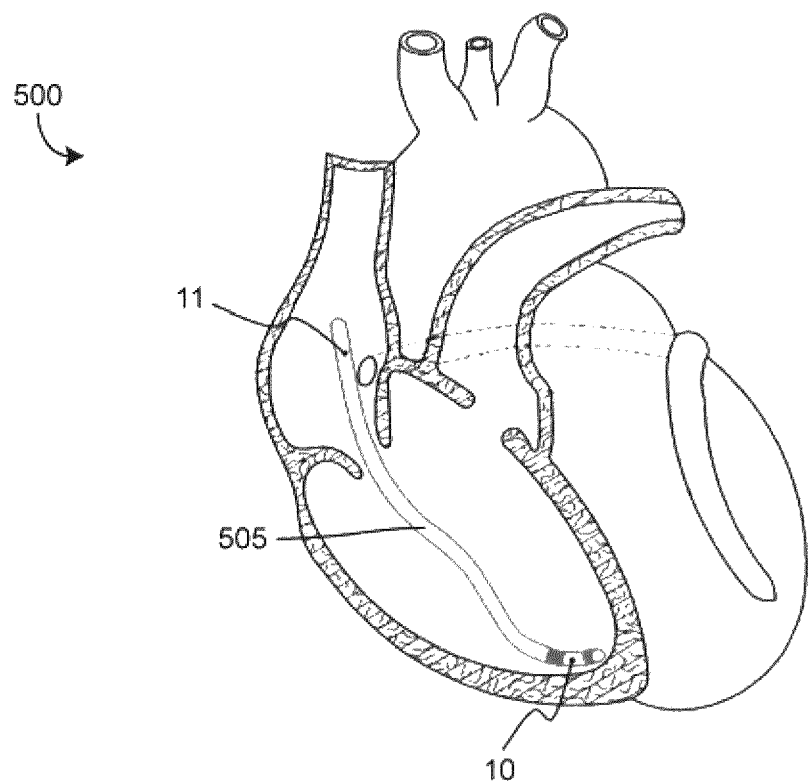
FIG. 5 is an illustration of a another example positioning of a wireless stimulation device having a single set of electrodes within a human body according to an exemplary embodiment.

In some embodiments, a wireless stimulation device may include electrodes proximate to only one end of the device and may be configured to stimulate only one chamber of the heart. For example, FIG. 5 illustrates a wireless stimulation device 505 having electrodes proximate to a first end 10 but no electrodes proximate to a second end 11 and being positioned within the vasculature at a position 500. In position 500, the electrodes proximate to first end 10 may be configured to pace the RV. In some such embodiments, the wireless stimulation device may still span across multiple sections of the vasculature. The increased length of the device as compared to other shorter single electrode set stimulation devices may allow a device such as device 505 to more efficiently transfer and convert signals received from a transmitter device into electrically energy for use in pacing the single chamber and/or may provide other benefits such as increased generation of electrical energy by an energy harvesting circuit.

Figure 6:
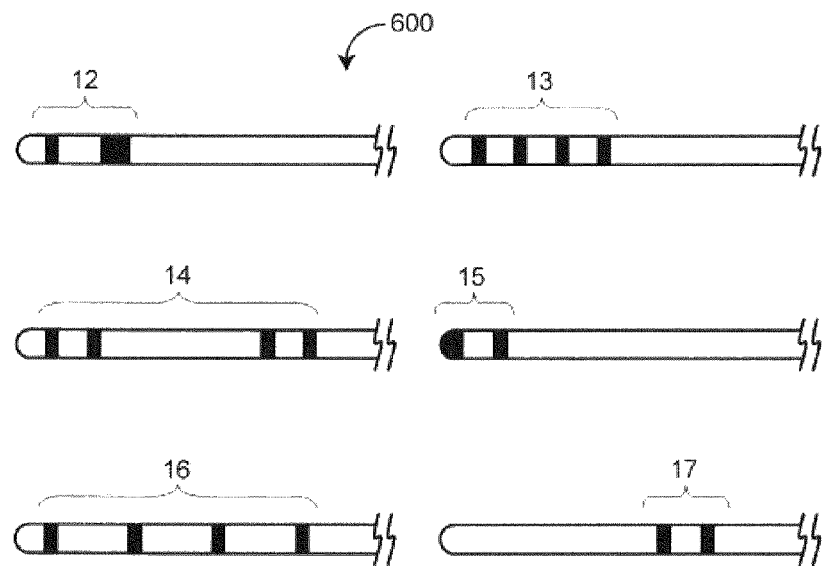
FIG. 6 is an illustration of a plurality of different example electrode configurations on a wireless stimulation device according to exemplary embodiments.

The wireless stimulation device may have a variety of different electrode configurations according to various exemplary embodiments, each of which may be configured to support different pacing schemes. FIG. 6 illustrates several different electrode configurations 600 that may be utilized by a wireless stimulation device such as device 100. FIG. 6 illustrates one end of a wireless stimulation device in a straightened configuration having several different electrode configurations. It should be understood that a stimulation device may have the illustrated configurations on both ends according to exemplary embodiments. In some embodiments, the two ends of the device may be symmetrical or equivalent, having the same configuration on both ends. In other embodiments, different configurations may be used on each end. Any potential combination of number, size, location, shape, and other characteristics of the electrodes (e.g., at each end) is contemplated within the scope of the present disclosure.

In some embodiments, such as those illustrated in FIG. 6, the electrodes may be in the form of cylindrical rings. The electrodes may be made of any material that is suitable for long-term implantation within the human body. In some embodiments, the electrodes may include an outer surface coating or other features designed to improve their electrical performance. The specific shape, material, appearance, surface area, surface finishing, electrical properties, and/or other characteristics of the electrodes may vary according to various exemplary embodiments, and all such embodiments are contemplated within the scope of the present disclosure.

In a first electrode configuration 12, a pair of electrodes is located in proximity to the tip of the body end. A first electrode in the pair may have a smaller surface area compared to a second electrode in the pair. The smaller electrode may be used as the cathode and the larger electrode may be used as the anode in the stimulation circuit.

In a second configuration 13, multiple electrodes may be disposed along the body end (e.g., at equal distances from one another and positioned near the tip of the end). One or more pairs of the electrodes may be selected from among the several possible combinations for pacing.

In a third configuration 14, multiple pairs of electrodes may be located in different segments of the device (e.g., one pair in a first segment and a second pair in a second segment). This may allow simultaneous or sequential pacing between pairs of electrodes, for example, under control of a controller incorporated in the wireless stimulation device.

In a fourth configuration 15, a first electrode may be located on the tip of the body end rather than having a cylindrical or annular shape. An electrode oriented on the tip of the body end may be utilized in any of the other configurations shown in FIG. 6.

Figure 13:
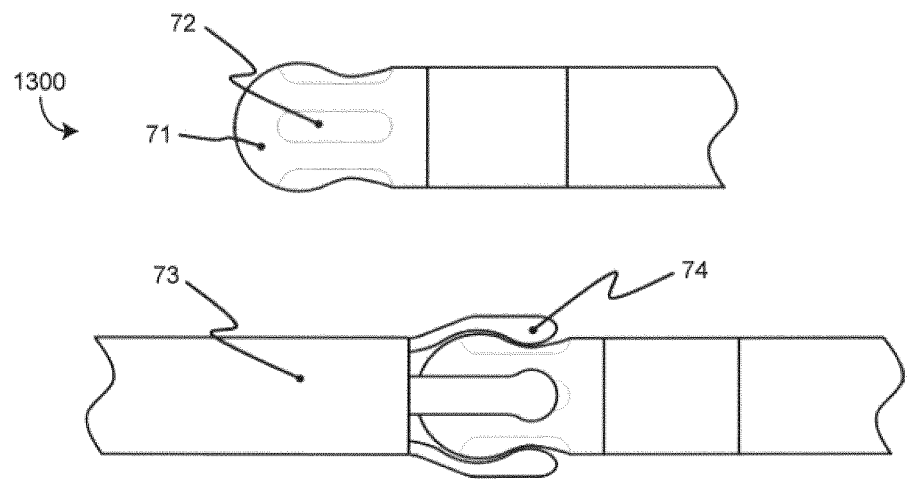
FIG. 13 is an illustration of a deployment system for deploying a wireless stimulation device into the body of a patient according to an exemplary embodiment.

In a fifth configuration 16, multiple electrodes are disposed along the body as in FIG. 13 but are distributed over a longer segment of the body, rather than more concentrated near the tip of the end. This may allow for pacing of more distant sites within the same cardiac chamber.

In a sixth configuration 17, a number of electrodes may be located relatively far from the device end in order, for example, to target specific stimulation sites. While various exemplary configurations are shown in FIG. 6 for the purposes of illustration, it should be understood that many other configurations may be utilized for electrode positioning on the body of the wireless stimulation circuit, and all such configurations are contemplated within the scope of the present disclosure.

Figure 7:
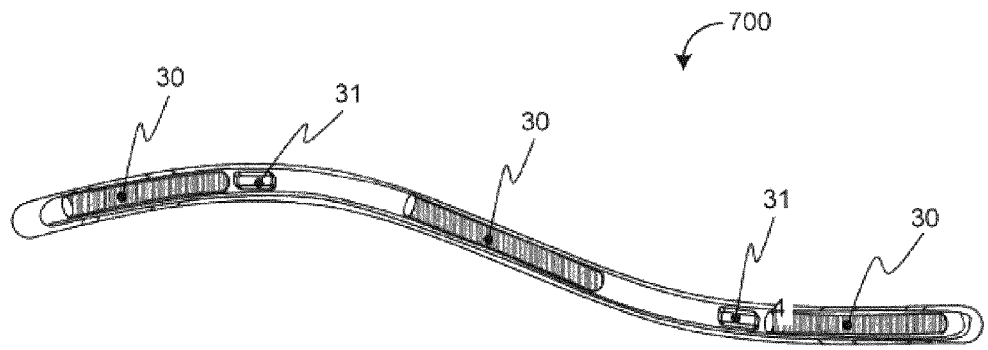
FIG. 7 is an illustration of an example power system that may be used by the wireless stimulation device of FIG. 1 to convert signals received from a transmitter device into power for use in providing stimulation according to an exemplary embodiment.

FIG. 7 shows an illustration receiver circuit 700, according to an exemplary embodiment, which may be employed by device 100 to convert signals received from a transmitter device into electrical power, for use in providing stimulation. Device 100 is configured to be implanted intracardially and to operate without being physically connected with other devices. In some embodiments, device 100 may be deployed in or near the heart via venous access (e.g., like a traditional pacemaker or defibrillator electrocatheter implant). In some embodiments, device 100 may be compatible with implant in a coronary vein through coronary sinus access.

For implantation in the targeted sites, device 100 may have to satisfy certain dimensional constraints. The diameter and/or internal volume of body 1 may be limited by the dimensions of the implantation site, while the length of body 1 may be somewhat more flexible.

In order for device 100 to deliver electrical stimuli to the heart, an energy source is incorporated internally to device 100. The energy source may include one or more of a variety of devices. For instance, batteries are a widely used power source for electronic devices. In various embodiments, various types of batteries may be used as a power source provided they are compatible with long-term implantation. Batteries by themselves may be inadequate to both satisfy the dimensional requirements of device 100 and provide enough energy to power device 100 for an acceptably long period of time.

To meet the energy requirements within the confined space of body 1, device 100 may include a receiver circuit configured to receive wireless signals from a transmitter device and convert the signals into electrical energy that can be used to provide pacing stimuli. The transmitter device may be located in physical proximity to device 100, either implanted subcutaneously or positioned external to the patient's body. The transmitter may be powered by an energy source such as a battery and may be capable of radiating energy through signals that may be received by device 100. Device 100 may extract energy from the signals (e.g., fields) generated by the transmitter and convert it into a form, such as electrical energy or power, that may then be used to deliver electrical stimuli to the cardiac tissue. In some embodiments, the power generated from the received signals may additionally or alternatively be used to power one or more components (e.g., a processing or controls circuit) of device 100.

In various embodiments, one or more of several different methods may be used for transferring energy between the transmitter and wireless stimulation device 100. In some embodiments, energy may be transferred from the transmitter to device 100 using electromagnetic induction. In some embodiments, energy may be transferred using resonant inductive coupling or electrodynamic induction. The transmitter and the stimulation device may each include one or more magnetic coils that are tuned to resonate at the same frequency. The transmitter coil may then be driven with an oscillating current to generate an oscillating magnetic field. The coil of the stimulation device, which is tuned to the same resonant frequency as the coil of the transmitter, absorbs the energy signals from the field generated by the transmitter. The energy can be converted into electrical power for use in providing stimuli using a number of different methods, such as rectifying and regulating the AC energy from the coil to generate a DC voltage.

In some embodiments, energy may be transferred between the transmitter and device 100 using electromagnetic radiation. In some embodiments, the energy may be transferred using microwave radiation. The transmitter may include a signal generation circuit configured to generate a microwave signal and an antenna configured to transmit the microwave signal in one or more directions. The antenna may be oriented in a fashion to direct the microwave signal towards an antenna of the stimulation device. The antenna of the stimulation device is configured to receive the microwave signal and convert the microwave signal into electrical power for use in providing stimuli. In some embodiments, the antenna of the stimulation device may be a rectifying antenna, or rectenna, configured to receive the microwave signal and rectify the signal to obtain a DC voltage.

In some embodiments, the energy may be transferred using electromagnetic radiation in the visible or invisible region of spectrum. For example, the transmitter may be equipped with a light emitter, such as a laser, that is directed at a receiver device, such as a photovoltaic cell, of the stimulation device. The receiver device may be configured to receive energy through the detected visible or invisible light and convert the energy into electrical power.

In some embodiments, energy may be transferred between the transmitter and device 100 using acoustic radiation. For example, the transmitter may generate ultrasound waves or shock waves and propagate the waves towards the stimulation device using an antenna. The stimulation device may include an antenna and receiver circuit configured to detect the acoustic waves, generate a signal (e.g., AC waveform) from the waves, and convert the signal into electrical power (e.g., a DC voltage, such as through rectification) for use in providing stimuli.

FIG. 7 illustrates an exemplary embodiment in which device 100 receives power from the transmitter via inductive coupling. The transmitter incorporates one or more magnetic coils and a generation circuit configured to generate a magnetic field in the surrounding space using the coils, for example, by forcing an oscillating current through the coil(s). Various different frequencies, modulation schemes, field amplitudes, etc. may be utilized by the transmitter.

Receiver circuit 700 of the implanted wireless stimulation device includes one or more magnetic coils 30 suitable for extracting energy from the magnetic fields generated by the transmitter. Coils 30 are electrically connected (e.g., by microcables) to one or more conversion devices 31 (e.g., electronic circuits) configured to extract or convert the energy from the coils into electrical power that may be used for providing stimuli (e.g., through rectification). In some embodiments, the extracted power may be stored in an energy storage device (e.g., a battery or capacitor) for later use in providing stimuli and/or powering components of the stimulation device. In some embodiments, conversion devices 31 may be connected (e.g., directly) to electrodes and the transmitter may directly drive the stimulation process rather than circuitry onboard the stimulation device.

In some embodiments, a stimulation device having a relatively long body may be equipped with multiple coils 30 distributed along its length. The power extracted by each individual coil may be additively combined with that coming from the other coils. When a single coil is used, even with a length equal to the total length of the receiver, it is possible that the electromagnetic force induced in different sections of the coil may cancel out (e.g., in part or entirely) and little or no energy may be extracted. Such a cancellation effect may occur, for example, if the receiver is significantly bent so that different parts of the long coil are oriented differently with respect to the transmitted field. Such bending may occur, for example, if the receiver is implanted in a tortuous branch of the coronary tree. By using several separate coils and summing the power extracted from each coil rather than the current induced in each single coil, this cancellation effect may be significantly reduced and the overall energy transfer efficiency may be increased. This may allow the battery in the transmitter to last longer and/or allow for a smaller battery to be utilized to power the transmitter. This advantage may be similar to the concept of "diversity" in telecommunications systems.

In some embodiments, the transmitter and receiver may have multiple sets of paired coils tuned to different frequencies to separately control energy transmission to different parts of the stimulation device. For example, a transmitter may have a first coil that is matched to (e.g., has a same resonant frequency as) a first coil of the stimulation device that is connected with a first set of electrodes on one end of the stimulation device. The transmitter may have a second coil that is matched to a second coil of the stimulation device that is connected with a second set of electrodes on an opposite end of the stimulation device. The transmitter may be able to separately control the transmission of power to drive the first set of electrodes and the second set of electrodes by separately driving the first coil and the second coil of the transmitter.

In some embodiments, the stimulation device may be equipped with one or more of several forms of on-board energy generators, such as energy scavenging or energy harvesting circuits. Such energy harvesting circuits may generate some or all of the power needed to power components of the stimulation device and/or provide stimulation to the cardiac tissue internally (e.g., without using power received through signals from the transmitter). One example harvesting circuit may be configured to convert flexural motion (e.g., motion generated during the cardiac cycle) into electrical energy. Other harvesting circuits may utilize other features or conditions internal to the stimulation device and/or the body to generate electrical energy. In some embodiments, a harvesting circuit may utilize triboelectric effects of polymers in the device. Bending of the receiver may create frictions that results in electrical charges being generated at the poles of a conversion element.

Figure 8:
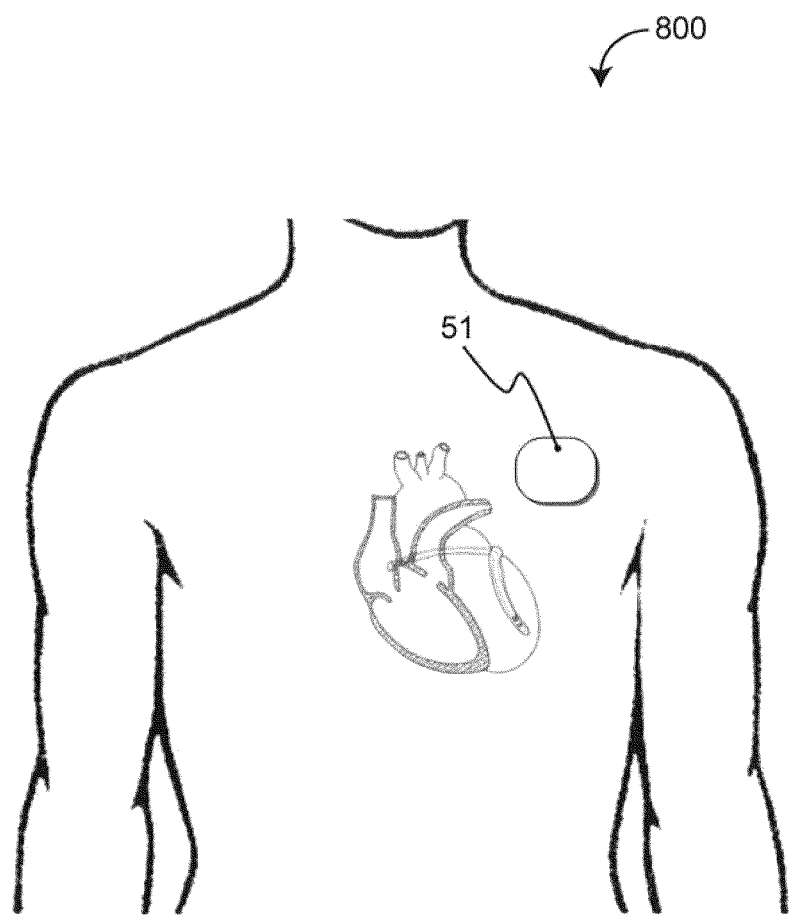
FIG. 8 is an illustration of an example position for a transmitter device with respect to the heart according to an exemplary embodiment.

With reference to FIG. 8, an illustration is shown according to an exemplary embodiment of a positioning of transmitter device 51 with respect to an implanted wireless stimulation device. Transmitter device 51 may include an energy storage device, such as a battery, and may be configured to generate electromagnetic fields in surrounding space by which energy may be transferred to the stimulation device. In the illustrated exemplary embodiment, transmitter device 51 may be enclosed in a hermetic can and may be implanted subcutaneously at a relatively short distance from the stimulation device (e.g., in the chest region, as is commonly done for pacemakers and implantable defibrillators). Since no physical connection exists between the subcutaneously implanted transmitter device 51 and the stimulation device, the invasiveness and complexity of the implant maneuver, particularly for the transmitter device, can be reduced. Replacement of transmitter device 51 (e.g., when the battery has reached end of life) may be simpler and less invasive to the patient because of the absence of electrodes to be disconnected from the old device and reconnected to the new device, with possible risks of complications and failures associated with this maneuver. The need to replace a device because of battery depletion is an issue frequently encountered with pacing devices.

In order to transmit energy and/or other information (e.g., control signals) to the stimulation device, transmitter device 51 may incorporate suitable transducers or other devices capable of converting battery power into fields or other signals, as described above according to various exemplary transmission methods. In some embodiments, the transducer may include one or more coils configured to generate electromagnetic fields in the space surrounding the transmitter. The current induced in the coils of the stimulation device may be rectified by an electronic circuit, and the energy may be made available for use in providing electrical stimulation. In other embodiments, transmitter device 51 may incorporate a transducer capable of generating fields of acoustic (e.g., ultrasonic) or other kinds of pressure waves in the patient's body. The stimulation device may include a similar transducer configured to generate electrical currents when immersed in such a mechanical vibration field, thus allowing the transfer of energy from the transmitter to the stimulation device.

Figure 9:
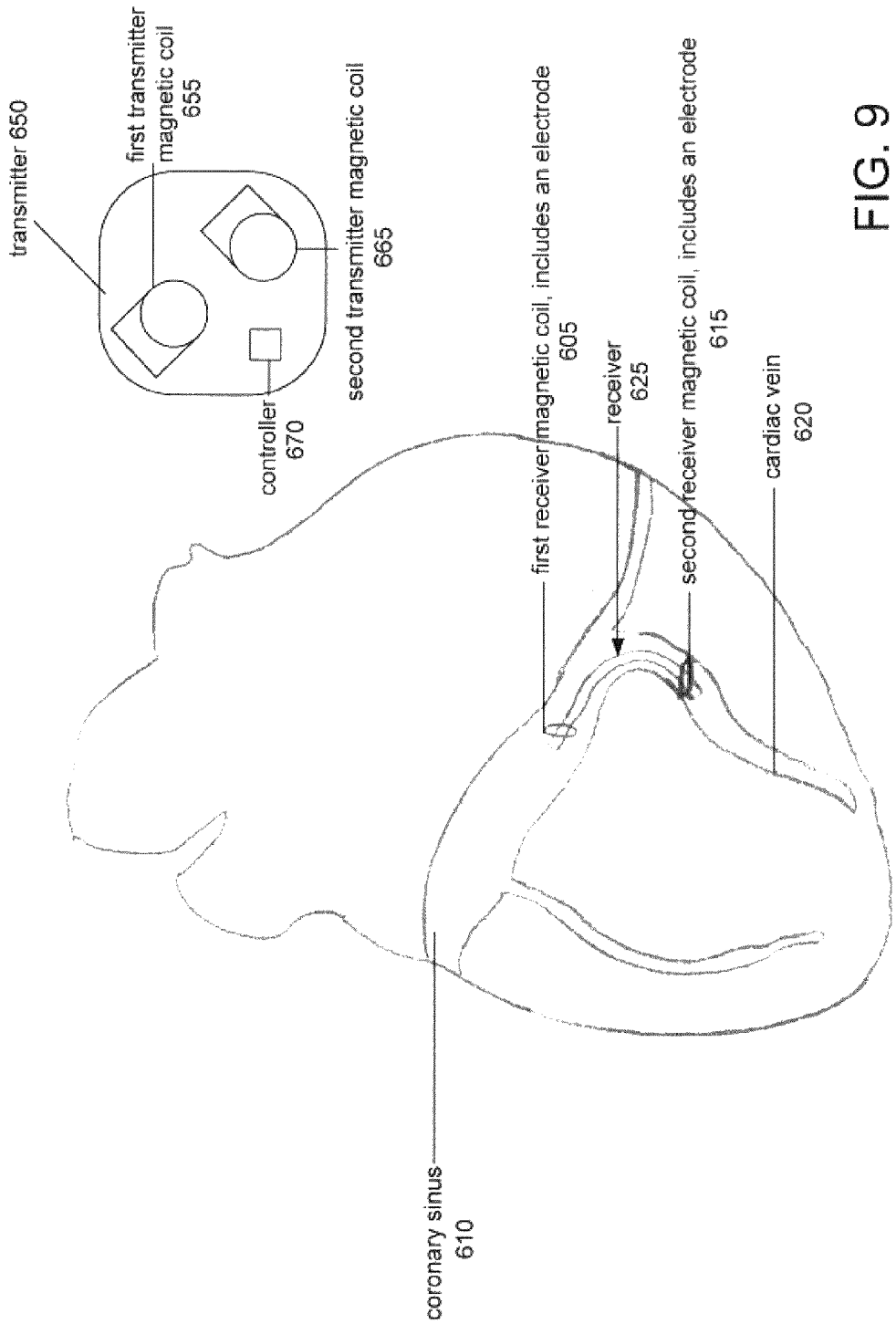
FIG. 9 is an illustration of an example configuration of a transmitter device and an implanted wireless stimulation device according to an exemplary embodiment.

FIG. 9 illustrates a transmitter 650 and receiver 625 (e.g., implanted stimulation device) configured to transmit energy through electromagnetic induction according to an exemplary embodiment. Receiver 625 includes a first receiver magnetic coil 605 configured for placement, for example, in a coronary sinus 610 and a second receiver magnetic coil 615 configured for placement, for example, in a cardiac vein 620. Coils 605 and 615 include or are coupled to electrodes configured to provide electrical stimuli to cardiac tissue proximate to the electrodes. In the illustrated exemplary embodiment, first receiver coil 605 is oriented substantially perpendicular to second receiver coil 615.

Transmitter 650 includes a first transmitter magnetic coil 655 and a second transmitter magnetic coil 665. Transmitter coils 655 and 665 are configured to interact with, and selectively induce a current in, receiver coils 605 and 615, respectively, to effect dual-chamber pacing. First transmitter coil 655 may be paired with first receiver coil 605 due to their relative positioning, such that the magnetic field generated upon activation of first transmitter coil 655 is, at the location of first receiver coil 605, substantially parallel to the transverse axis of first receiver coil 605. The magnetic field generated by first transmitter coil 655 induces a current in first receiver coil 605 when the strength of the magnetic field is cause to change with time. At the location of second receiver coil 615, the magnetic field generated by first transmitter coil 655 is substantially orthogonal to the transverse axis of second receiver coil 615, and the field generated by first transmitter coil 655 induces substantially little or no current in the second receiver coil when the strength of the field is caused to change with time. Second transmitter coil 665 and first and second receiver coils 605 and 615 are correspondingly oriented such that the time-varying magnetic field generated by second transmitter coil 665 induces current in second receiver coil 615 but substantially no current in first receiver coil 605. The transverse axes of first transmitter coil 655 and second transmitter coil 665 are substantially orthogonal to one another.

Transmitter 650 includes a controller 670 configured to control transmitter coils 655 and 665 to provide time-varying magnetic fields. In some embodiments, coils 655 and 665 may be activated alternately. Multiplexing between the first and second transmitter coils may achieve pair-wise activation of the respective receiver coils 605 and 615, and a voltage may be induced between electrodes associated with coils 605 and 615. Controller 670 may operate according to an algorithm for pacing the heart and may be attached to a power source such as a battery.

Figure 10:
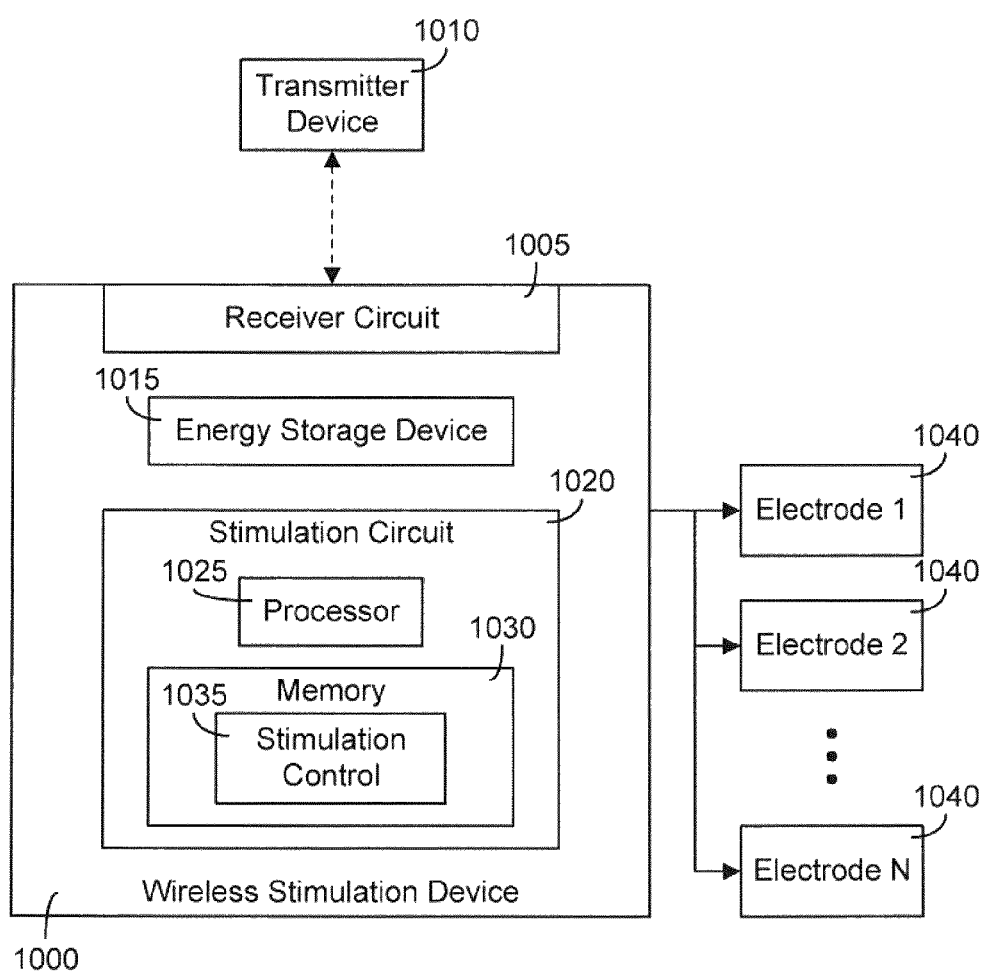
FIG. 10 is a block diagram of a wireless stimulation device according to an exemplary embodiment.

Referring now to FIG. 10, a block diagram of a wireless stimulation device 1000 is shown according to an exemplary embodiment. Device 1000 is configured to receive power signals wirelessly from a transmitter device 1010 and use the power signals to generate electrical power for driving one or more electrodes 1040 to stimulate cardiac tissue.

Device 1000 includes a receiver circuit 1005 that is configured to receive the signals from transmitter device 1010 and convert the signals into electrical power. Receiver circuit 1005 may include one or more coils used to receive the signals (e.g., to extract energy from fields generated by transmitter 1010) and one or more devices (e.g., electrical circuits, such as rectification circuits) used to convert the receiver signals into electrical power (e.g., DC voltage) that may be used to drive electrodes 1040. In some embodiments, receiver circuit 1005 may be connected (e.g., directly) to electrodes 1040 and may drive the provision of stimulation based on the signals received from transmitter device 1010. In some embodiments, receiver circuit 1005 may store the extracted electrical power in an energy storage device 1015 for later use in driving electrodes 1040 and/or powering components of device 1000.

In some embodiments, device 1000 may include a stimulation circuit 1020 configured to control the provision of stimulation by electrodes 1040 using energy from energy storage device 1015. Stimulation circuit 1020 may include a processor 1025 (e.g., any general purpose or special purpose processor suitable for inclusion within device 1000) and a memory 1030 (e.g., any machine-readable medium suitable for inclusion within device 1000).

Memory 1030 may include a stimulation control module 1035 (e.g., machine-executable instructions stored in memory 1030) configured to control various parameters of the stimulation provided by device 1000. For example, stimulation control module 1035 may control the timing, magnitude, and/or other parameters associated with the stimulation provided by device 1000. In some embodiments, stimulation control module 1035 may control the stimulation according to one or more pacing schemes reflected in algorithms stored in memory 1030. Different pacing control may be utilized by stimulation control module 1035 depending on the implant location of device 1000. In some embodiments, memory 1030 may include a sensing module configured to control electrodes 1040 to measure parameters related to the surrounding cardiac tissue, such as whether capture has occurred subsequent to stimulation.

In some embodiments, signals received from transmitter device 1010 may include one or more data signals or signal portions configured to control or modify one or more parameters of the stimulation provided by device 1000. In some such embodiments, at least some of the timing and control logic used to control the stimulation provided by device 1000 may be located in transmitter device 1010 rather than or in addition to device 1000. In one embodiment, device 1000 may provide a stimulus upon receiving a command to do so from transmitter device 1010, and transmitter device 1010 may control the frequency, pulse amplitude, shape, polarity, duration, etc. of the stimulation provided by device 1000 by controlling the commands sent to device 1000. In some embodiments, data from transmitter device 1010 may be encoded (e.g., using modulation) within the power signals provided by transmitter device 1010. In some embodiments, the data may be transmitted in separate transmissions from the power signals/fields. In various embodiments, the data may be transmitted using the same or different transmission methods (e.g., inductive coupling, electromagnetic radiation, acoustic radiation, etc.). In some embodiments, transmitter device 1010 may transmit data commanding that stimuli be provided by a subset (e.g., one or more) of several electrodes, and stimulation control module 1035 may decode the command and cause the identified subset of electrodes to provide stimulation. In some embodiments, encoded data signals may include reliability features, such as redundancy check, checksums, etc., to ensure a reliable transmission and response.

Energy storage device 1015 may include a battery, a capacitor, and/or any other type of energy storage device suitable for inclusion within an implantable stimulation device. In some embodiments, such as implementations in which device 1000 acts immediately upon commands from transmitter device 1010, only a short term energy storage device may be required (e.g., long enough to store energy for the time required to process the command and carry out the requested action, such as a few milliseconds). In some embodiments (e.g., implementations where at least some level of logic is stored in device 1000 that allows device 1000 to control stimulation independently of transmitter device 1010), a longer term energy storage device may be utilized to reduce the need for regular transmissions from transmitter device 1010 to power device 1000. In such an embodiment, data/commands from transmitter device 1010 may be used to configure certain parameters of stimulation control module 1035, such as selection of a particular pacing sequence, and the stimulation process may be executed (e.g., autonomously) by stimulation control module 1035 without further intervention by the transmitter other than to provide energy refills as needed.

Figure 11:
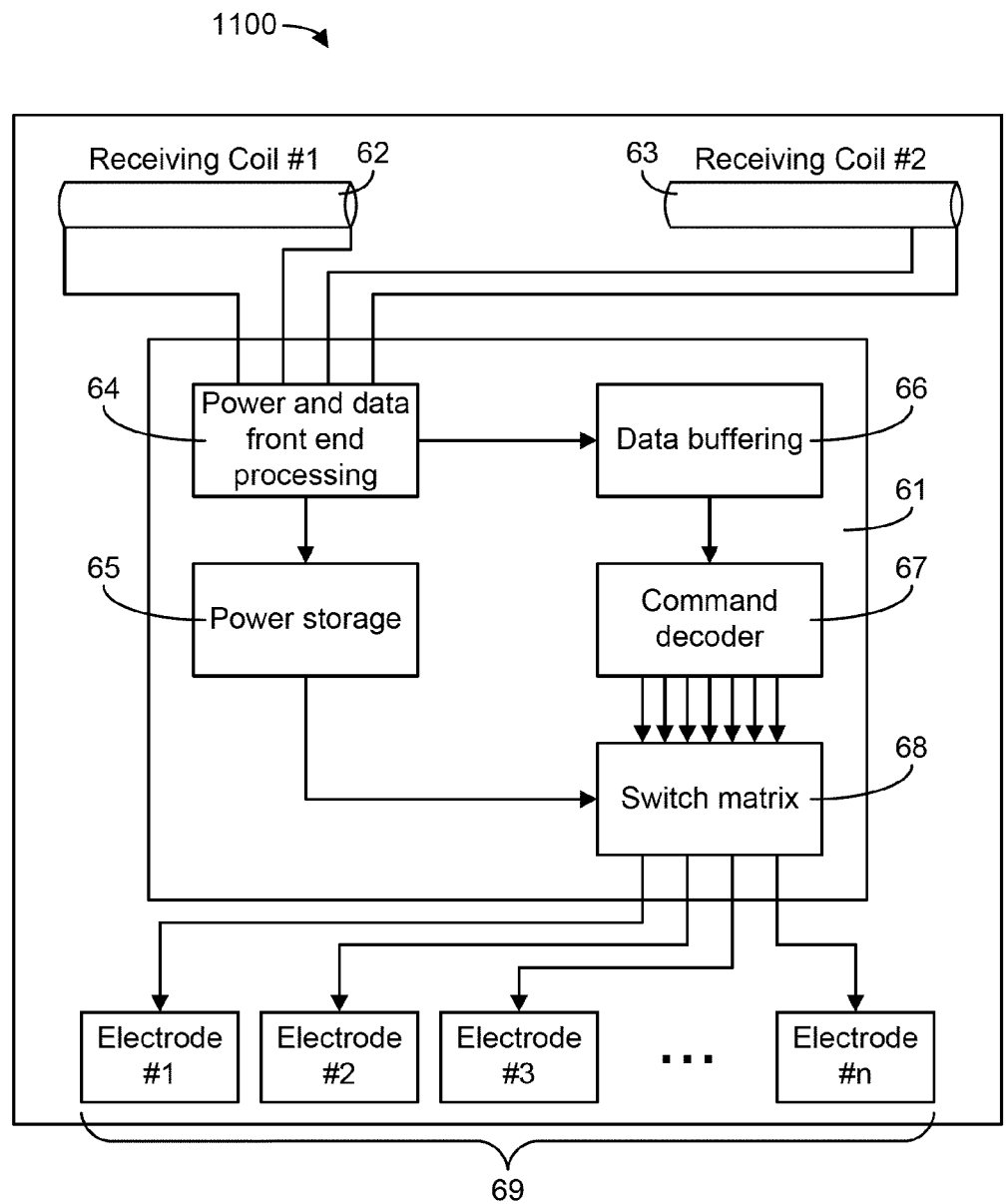
FIG. 11 is a more detailed block diagram of a wireless stimulation device according to an exemplary embodiment.

With reference to FIG. 11, a more detailed block diagram of a wireless stimulation device 1100 is shown according to an exemplary embodiment. A stimulation circuit 61 may include an electronic command processor configured to decode commands from a transmitter device and execute the commands accordingly, for example by selecting one or more pairs of electrodes between which a stimulus shall be delivered. To this effect, the field used to transmit the energy for the pulse may be modulated in one or more among several ways, such as, for example, by amplitude modulation, frequency modulation, pulse width modulation, etc. Any other field parameter that may be changed to convey information would be suitable for this purpose. Any of the parameters or combination of parameters associated to stimulation might be programmed in this way, such as the timing of the pulse(s), a particular sequence of pulses (in case a multisite stimulation is desired), the amplitude, the shape, the polarity, the duration of individual pulses, etc. Stimulation circuit 61 may decode the information received along with the energy for the stimuli, and then deliver the stored energy to the electrodes, for example according to a predetermined algorithm.

In the exemplary implementation illustrated in FIG. 11, the receiving elements might be two coils 62 and 63. A power and data front end processing module 64 may recover the power from each of the individual coils and may refill a power storage element 65 (which could be, for example, a suitable electric capacitor). The processing module 64 may (e.g., at the same time) separate the command information wirelessly transmitted along with the power and send the data stream to a buffering module 66, which might hold the data during the operational cycle of the receiver. The data may then be interpreted by a decoder module 67 which, in the example, drives a switch matrix 68 so that the stored pulse energy is delivered to the appropriate electrodes 69. In some embodiments, device 1100 may control pacing without using a control module having significant processing characteristics (e.g., when control logic has been placed instead in the transmitter). In some such embodiments, coils 62 and 63 may be directly connected to a particular pair of electrodes, so that each time the transmitter sends a pulse, the current induced in the coil is directly (or indirectly, such as through a rectifying device) delivered to the cardiac tissue. If more than one receiving device is present in the receiver, a method may be used to differentiate between the electrode pairs, such as by making the coils resonate at different specific frequencies and having the transmitter generate fields of relevant frequencies to activate the electrode pairs independently.

Figure 12:
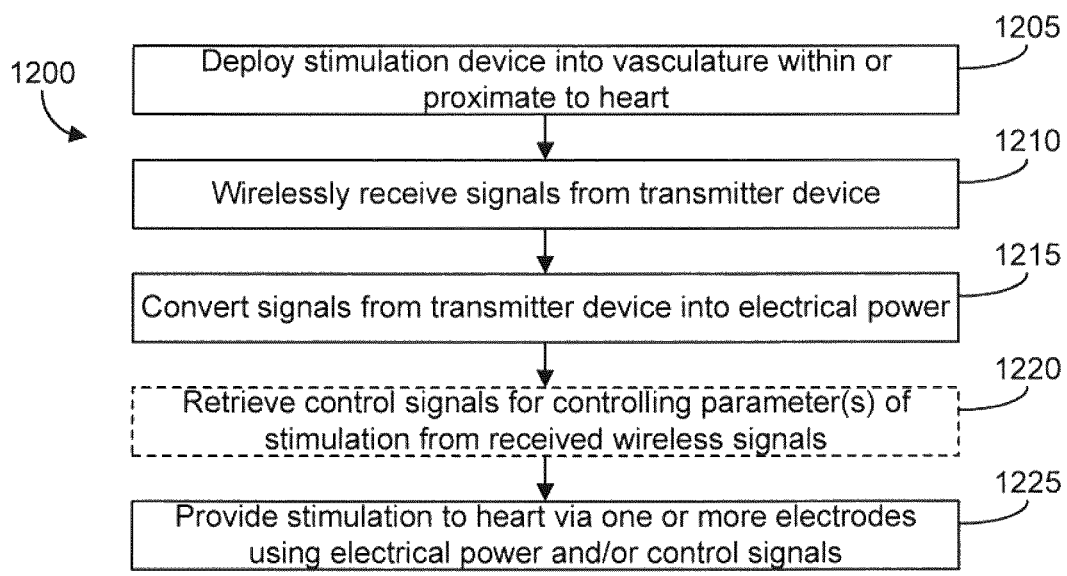
FIG. 12 is a flow diagram of a process for stimulating the heart using an implantable wireless stimulation device according to an exemplary embodiment.

In relation to FIG. 12, a flow diagram is shown, according to an exemplary embodiment, of a method 1200 for providing stimulation via an implantable wireless stimulation device. Method 1200 may be carried out by devices 100, 1000, 1100, and/or various other systems and devices described in the present disclosure.

A stimulation device may be deployed within the vasculature within or proximate to the heart, such as through venous access (1205). Once implanted, the stimulation device may receive signals wirelessly from a transmitter device (1210). In various embodiments, the signals may include power signals, data, or both. The signals may include electromagnetic and/or other fields sensed by a receiver circuit of the stimulation device. The receiver circuit may convert the signals from the transmitter device into electrical power for use in providing stimulation (1215). In some embodiments, the signals from the transmitter device may include one or more control signals for controlling one or more parameters of the stimulation to be provided. In such embodiments, the stimulation device may be configured to retrieve the control signals from the signals received from the transmitter device (1220). The stimulation device may then provide stimulation to one or more chambers of the heart via electrodes using the electrical power and/or control signals (1225).

With reference to FIG. 13, an example deployment device that may be used to deploy an implantable wireless stimulation device within the vasculature is shown according to an exemplary embodiment. The stimulation device may be implanted in or near the heart via transcutaneous (e.g., venous) access.

The deployment device may include a catheter 73 that may house a holding mechanism 74 able to hold the receiver, for example, by one or more prongs or other mechanisms able to grip or otherwise hold the device so as to enable the implanter physician to exert push, traction and torque forces as required to navigate the device through the desired implant site. Once in position, mechanism 74 may then be actuated so as to free the stimulation device and allow retraction of catheter 73 and holding mechanism 74. In some embodiments, holding mechanism 74 may be reconnected to the stimulation device without removing the stimulation device and/or deployment device from the body, should a repositioning be required at the time of implant. Thus detached, the receiver may remain fixed in the body by virtue of an active safety element, such as a stent, or a passive safety element, such as prongs or another type of anchor mechanism.

In the illustrated embodiment, a deployment attachment 71 on the tip of the stimulation device may have a ball-like shape and deployment catheter 73 may be equipped at the distal end with a number of flexible prongs 74 designed to engage and release deployment attachment 71. Such an arrangement may provide sufficient push and pull capability to support manipulation during the implantation. In order to transmit torque, deployment attachment 71 may, for example, be provided with recessed zones 72 or indentations that allow prongs 74 to transmit torque from the delivery catheter to the device when prongs 74 are in the locked position. Recessed zones 72 may assist the deployment device in advancing the stimulation device through the vasculature and/or rotating the stimulation device within the vasculature. Any other feature providing torque transmission would equally fall within the scope of the disclosure.

Figure 14:
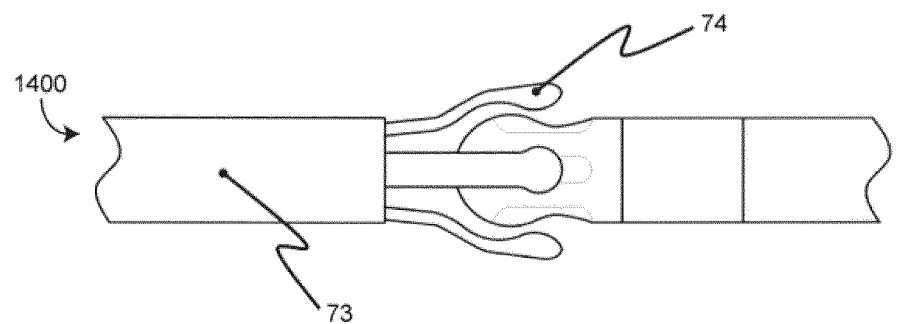
FIG. 14 is an illustration of the deployment system of FIG. 13 in which the deployment device is being disengaged from the deployment attachment of the wireless stimulation device according to an exemplary embodiment.

In order to release the receiver when the desired site has been reached, the sleeve of catheter 73 may be retracted slightly so that elastic prongs 74 may open, thus disengaging deployment attachment 71 as illustrated in FIG. 14. Any method of engaging and disengaging the deployment device and the stimulation device may be used as long as it responds to the function of holding and driving the receiver in order to reach a desired implant site.

Figure 15:
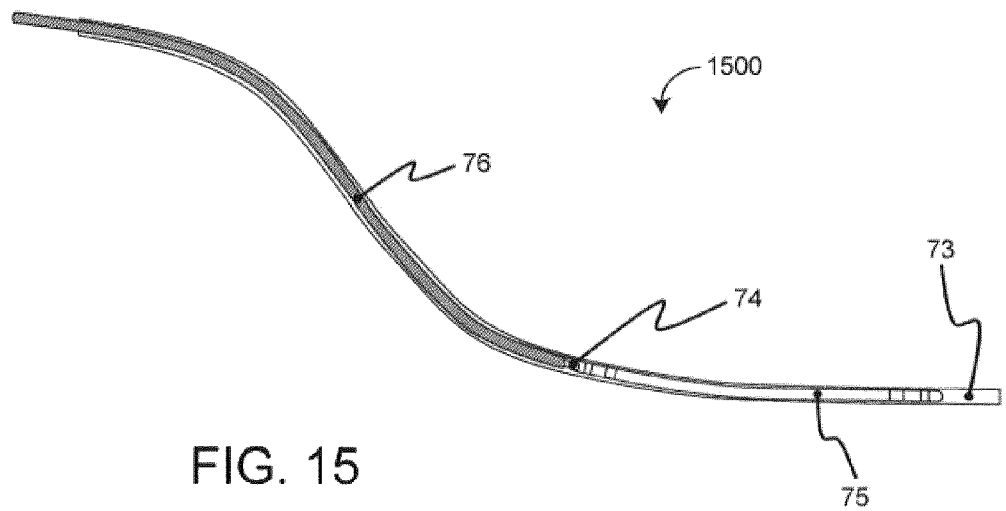
FIG. 15 is an illustration of an implementation of the deployment system of FIG. 13 in which the stimulation device is enclosed within a catheter during deployment according to an exemplary embodiment.

FIG. 15 illustrates an implementation of the deployment device of FIG. 13 in which a stimulation device 75 is contained within the sleeve of catheter 73. Prongs 74 and deployment catheter 73 may be designed in such a way that, while the receiver is being deployed, it remains inside the lumen of catheter 73.

Figure 16:
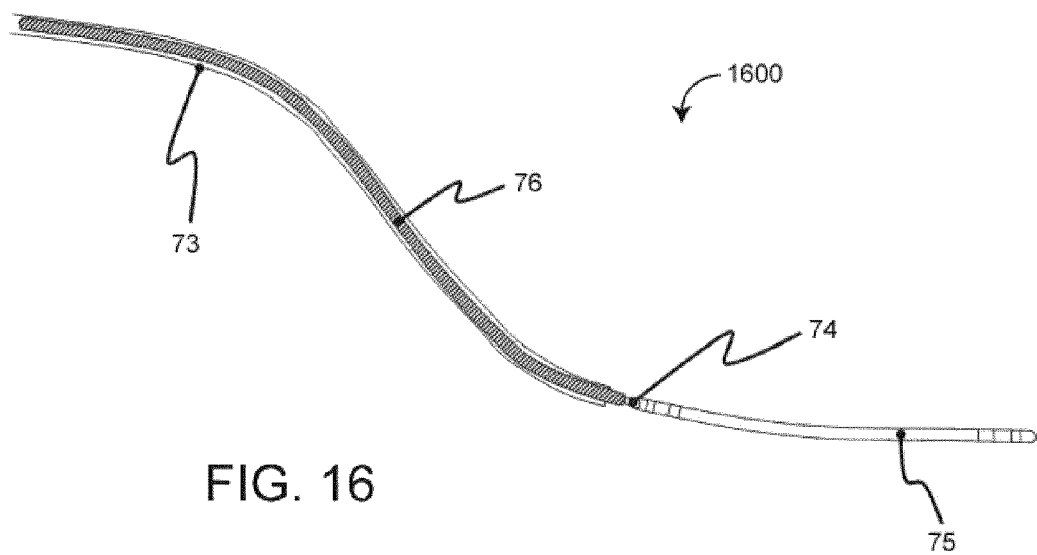
FIG. 16 is another illustration of the deployment system of FIG. 15 being used to deploy the wireless stimulation device in which an outer portion or sleeve is retracted to allow for placement of the wireless stimulation device according to an exemplary embodiment.

As it is shown in the exemplary embodiment, which depicts the configuration of the system while it is being advanced in the venous system of the patient, stimulation device 75 is entirely located inside the lumen of deployment catheter 73, while being held by prongs 74, which are part of a clamping catheter 76 and able to slide and rotate inside catheter 73, thus allowing clamping catheter 76 to manipulate stimulation device 75. According to this arrangement, deployment catheter 73 may be first advanced, for example, in the coronary sinus, then stimulation device 75, mated with the clamping catheter 76, may be inserted in the deployment catheter 73 and advanced up to its distal extremity, as illustrated in FIG. 15. When the desired position has been attained, the outer catheter 73 may then be partially refracted, for example, by sliding it backwards over stimulation device 75 and clamping catheter 76, exposing stimulation device 75, as shown in FIG. 16. At this point, if the position of the receiver is confirmed good, prongs 74 may be opened to release stimulation device 75.

In some embodiments, a physician may wish to reposition stimulation device 75 during an implantation procedure and again mate the deployment system with stimulation device 75 (e.g., to obtain a better implantation position). The delivery system may be configured such that it may newly engage the receiver without being removed from the body. This may be accomplished, in one exemplary embodiment, by advancing the deployment system towards the receiver so that prongs 74 are positioned over deployment attachment 71 as in FIG. 14. Prongs 74 may then be actuated in order to clamp stimulation device 75. In some embodiments, additional features may be incorporated to assist in coupling the deployment system to stimulation device 75, such as incorporating a magnet in the delivery mechanism and a metallic component in stimulation device 75 able to be attracted by the magnet.

In some embodiments, the holding mechanism may be designed to allow capturing of stimulation device 75 when deployment attachment 71 is not precisely coaxial with the delivery system. The illustrated deployment systems accomplish this function, as illustrated in FIG. 17. Such a feature may be accomplished by selecting an appropriate shape for prongs 74 and deployment attachment 71.

With reference generally to FIGS. 18A through 22, various anchoring features are shown, according to exemplary embodiments, that may be used to secure at least one portion of an implanted stimulation device in position within the vasculature, once a desired implantation site is reached. The structures presented in FIGS. 18A through 22 are illustrative of what can be used to anchor the stimulation device. Thus, other structures may be utilized in other embodiments, and all such embodiments fall within the scope of the present disclosure. Further, while the illustrated embodiments show one stabilization or anchoring structure, it should be understood that multiple structures may be used in some embodiments, e.g., one on each end of the stimulation device.

In relation to FIG. 18A, in one embodiment, a portion 80 of a stimulation device 75 may be semi-rigid and formed into a partially curved shape, such as an "S" shape. During deployment, portion 80 may be held straight (e.g., by a deployment catheter 81), as shown in FIG. 18B. Once catheter 81 is withdrawn, portion 80 returns to its original curved shape. This may help achieve stabilization of the device in certain cardiac sites, such as the coronary veins. If the receiver is located in a vein or other tubular structure in the heart with a diameter smaller than the side-to-side envelope of the "S", portion 80 may remain partially straightened, thus exerting an outwardly directed force or compression against the walls of the vessel. The friction generated between device 75 and the vessel may stabilize device 75. In some embodiments, the compression of device 75 against the walls of the vessel may help maintain good electrical contact between the electrodes and cardiac tissues, improving stimulation performance.

Figure 19:
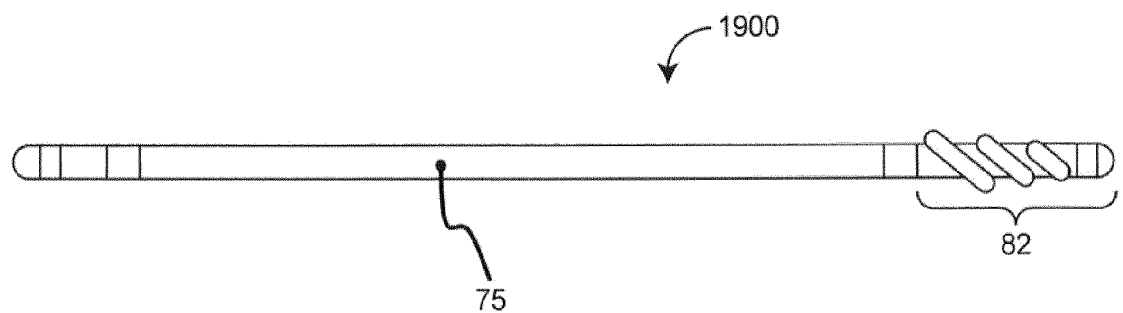
FIG. 19 is an illustration of a wireless stimulation device having a threaded anchoring attachment according to an exemplary embodiment.

FIG. 19 shows an exemplary embodiment in which device 75 includes a threaded attachment 82, such as a helicoidal feature. An outer diameter of threaded attachment 82 may be larger than an outer diameter of an adjacent portion of the body of device 75. Threaded attachment 82 may be wedged, for example, in a distal portion of a coronary vein and help maintain device 75 in position. In some embodiments, the threads of attachment 82 may be made of silicone. In some embodiments, shapes other than helicoidal shapes may be utilized for attachment 82 provided the shapes provide friction with the vessel wall.

Figure 20A:
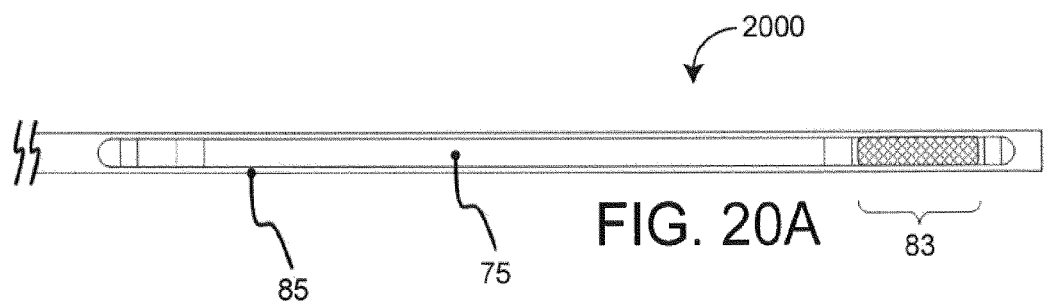
FIG. 20A is an illustration of a wireless stimulation device having a stent anchoring portion deployed within a deployment catheter according to an exemplary embodiment.
Figure 20B:
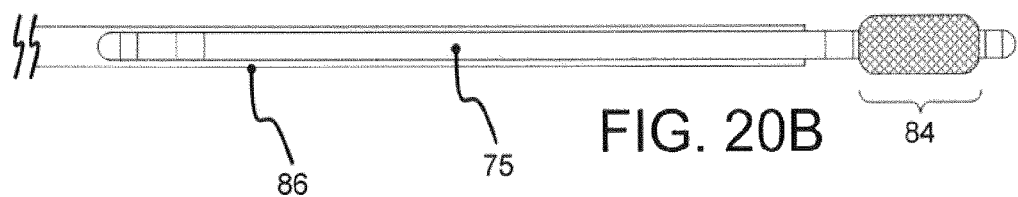
FIG. 20B is an illustration of the wireless stimulation device of FIG. 20A in which the deployment catheter has been retracted and the stent has expanded to hold the wireless stimulation device in place according to an exemplary embodiment.

FIG. 20A illustrates an exemplary embodiment in which device 75 includes a stent 83 or other stent-like feature. In FIG. 20A, stent 83 is kept retracted during deployment by a deployment catheter 85. Once catheter 85 is retracted as shown in FIG. 20B (see position 86), the stent is allowed to expand (see expanded stent 84), stabilizing the receiver in position. In some embodiments, the stent may be an active stent that is made electrically active, such that the stent may be connected to the stimulation circuitry of device 75 and utilized as one of the electrodes.

Figure 21:
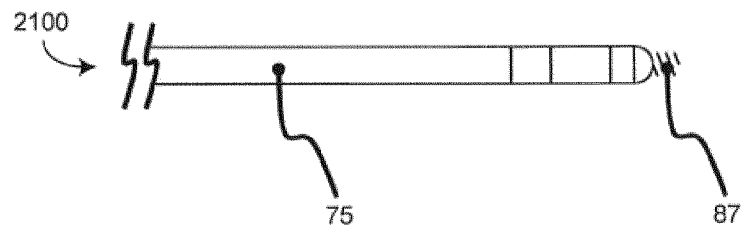
FIG. 21 is an illustration of a wireless stimulation device having a screw anchoring attachment configured to be threaded into cardiac tissue according to an exemplary embodiment.

FIG. 21 presents yet another exemplary embodiment, in which device 75 includes a helix attachment 87 (e.g., a screw portion) that may be screwed into the cardiac tissue to implant device 75. In some embodiments, helix attachment 87 may be made electrically active and used as an electrode.

Figure 22:
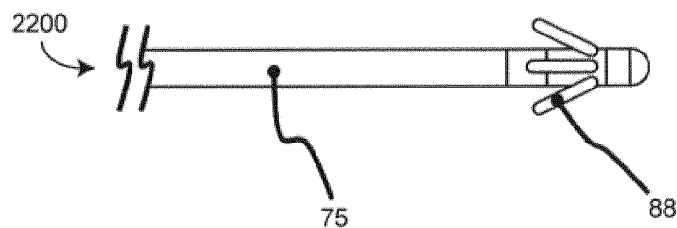
FIG. 22 is an illustration of a wireless stimulation device having a pronged anchoring portion according to an exemplary embodiment.

FIG. 22 illustrates another exemplary embodiment in which device 75 includes a pronged anchor 88. Pronged anchor 88 may be compressed against the body of device 75 during implantation by a deployment catheter and expanded once the implant site has been reached by retracting the catheter.

Figure 23:
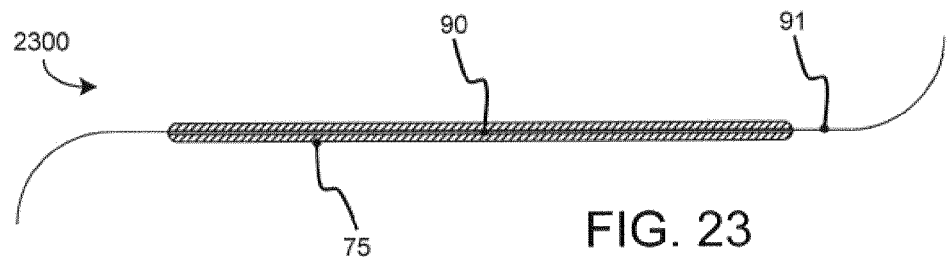
FIG. 23 is an illustration of a wireless stimulation device configured to be deployed using a guiding wire according to an exemplary embodiment.

With respect to FIG. 23, an exemplary embodiment is shown in which device 75 is deployed using a guiding wire 91. Device 75 may include a longitudinal hollow lumen 90 allowing device 75 to freely slide over guiding wire 91 during deployment. This allows device 75 to be deployed Over-The-Wire (OTW). Guiding wire 91 may first be positioned in the desired branch of the coronary tree and then be used to guide the receiver to the selected site.

Figure 24:
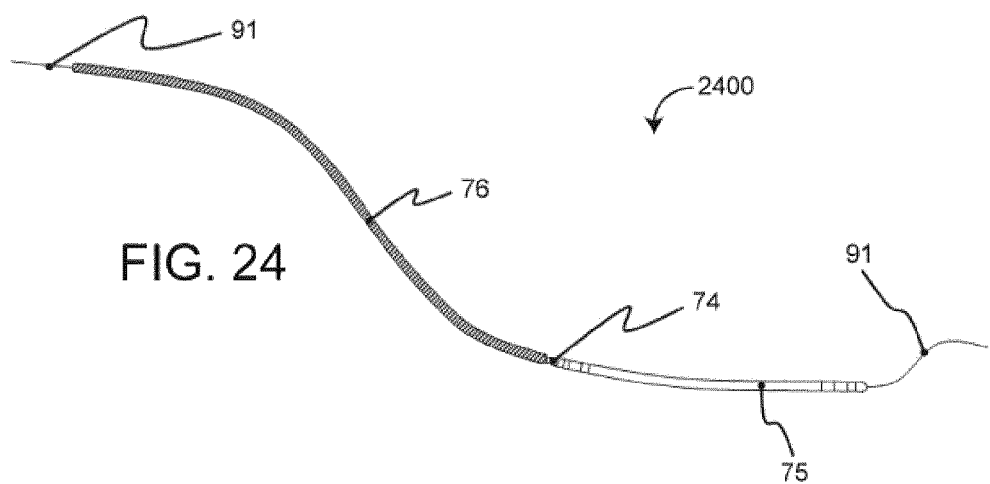
FIG. 24 is an illustration of the wireless stimulation device of FIG. 23 being deployed using a guiding wire and a deployment device according to an exemplary embodiment.

A deployment device such as those described above may be used to advance device 75 toward the selected site, as shown in FIG. 24. In the illustrated embodiment, device 75 may be mated with a holding catheter 76 by means of a holding mechanism 74 in one of the ways described above. Holding catheter 76 and holding mechanism 74 allow a guiding wire 91 to be inserted through the entire length of holding catheter 76 and device 75 so as the whole system may be able to slide freely over guiding wire 91. Holding catheter 76 may be used to push device 75 into the desired site, where device 75 may be left by disengaging holding mechanism 74 as previously described. If repositioning of the receiver 75 is required while, although separated, both device 75 and holding catheter 76 are still on guiding wire 91, a user may advance holding catheter 76 until device 75 may be clamped again. This can simplify the reengaging operation in that the axial alignment between device 75 and holding catheter 76 may be ensured by guiding wire 91.

In some embodiments, a wireless stimulation device according to any of the exemplary embodiments described herein may, in addition to providing pacing capabilities, provide sensing capabilities as well. The stimulation device may detect spontaneous or induced electrical potentials in the heart and modify stimulation behavior based on the detected signals. The sensed data may be processed locally in the stimulation device or remotely (e.g., in the transmission device). In some embodiments, the stimulation device may also be able to sense other properties as well, such as temperature, pressure, acceleration, concentration of chemical compounds, etc.

In some embodiments, the wireless stimulation device may be configured to transmit data (e.g., measurements from the sensors) to a remote device such as the transmitter device (e.g., through generated electromagnetic waves). The transmitted information may include sensor data, status data relating to the implanted device (e.g., amount of stored energy), and/or other information. In some embodiments, the same structures (e.g., transceivers, transducers, etc.) used to receive signals from the transmitter device may be used to transmit the data.

In some embodiments, a wireless stimulation device according to any of the exemplary embodiments described herein may be configured to be compatible for operation during a magnetic resonance imaging (MRI) operation. Traditional pacing leads conduct electrical currents for pacing and sensing using metallic conductors (e.g., cables or coils) running through the entire length of the lead. When these leads are immersed in the electromagnetic fields generated by an MRI scanner, large currents may be induced in the conductors, which may be dangerous to the patient because the cardiac tissues in contact with the electrodes of the lead may be heated up to the point where irreversible damage may occur.

In some embodiments of the stimulation device of the present disclosure, the length of the conductors connected to the pacing electrodes may be significantly shorter in comparison to a pacing lead, and currents induced by the MRI fields may be reduced, to the point that their effects become substantially lower or even negligible. In some of the implementations described above, the stimulation device has provision for electrode switching under control by one or more dedicated modules in the receiver. In some embodiments, the switches may, for example, be located in very close proximity to each of the electrodes (for example, each electrode may actually be integrated in an independent switching module). In such a case, there would be very little conductor of any appreciable length directly connected to the electrodes. For example, the stimulation device could be designed so that, in the presence of a large electromagnetic field such as those associated to MRI equipment, all the switches are simultaneously opened, reducing or eliminating the risks associated with tissue heating caused by "antenna effect" of conductors.

In some embodiments, the stimulation device may be configured such that it may be implanted in a mixed intracardiac/extracardiac environment. For example, the device may have a long, worm-like structure in which one end is implanted within or near the heart and the other end extends away from the heart. The external end may be positioned, for example, in the pulmonary artery or femoral vein. In some embodiments, the external end may be equipped with a pressure sensor for monitoring pulmonary artery pressure (related to an important hemodynamic parameter, the Pulmonary Capillary Wedge Pressure). In some implementations, the extracardiac end may be equipped with electrodes that may be used for rheographic measurements. Rheographic measurements may be performed by measuring the electrical resistance or impedance between two spatially distant points of a medium. This may be accomplished by injecting a known electrical current, through a portion of the volume of the medium between two spatially distant electrodes, and then measuring the voltage developed across the same terminal, or vice versa (i.e., applying a known voltage and measuring the current). Such measurements may be useful for determining the amount of fluid accumulated in the lungs, which is a symptom of acute cardiac decompensation. Thus, if the spatially separate electrodes are, for example, two electrodes at opposite ends of the device, and if the volume involved by the electrical current includes at least part of the lung tissue, then it is possible to detect variations in the amount of interstitial fluid accumulated in the lungs by detecting variations of the measured impedance (e.g., the higher the fluid contents, the lower the electrical impedance). Early detection of acute cardiac decompensation may allow for the delivery of a suitable therapy and avoid degeneration of the situation.

In some embodiments, the device may include a pair of large-surface electrodes. For example, the device may be used to defibrillate the heart, whereby one of the electrodes may be placed in the Superior Vena Cava (SVC) and another in proximity of the left heart through the coronary sinus, so as to allow generation of the large field required to shock the tissue.

The foregoing disclosure makes reference to drawings. As noted above, these drawings illustrate certain details of specific embodiments that implement the systems, methods, and programs set forth in the disclosure. However, referencing the drawings in this disclosure should not be construed as imposing on the disclosure any limitations that may be present in the drawings. The disclosure contemplates implementing the described methods, systems, and program products on any machine-readable media for accomplishing its operations. The disclosed embodiments may be implemented using an existing computer processor, or by a special purpose computer processor incorporated for this or another purpose or by a hardwired system. No claim element herein is to be construed as invoking "means plus function" language unless the element is expressly recited using the phrase "means for." Furthermore, no element, component or method step in the present disclosure is intended to be dedicated to the public, regardless of whether the element, component or method step is explicitly recited in the claims.

As noted above, embodiments within the scope of the present disclosure include program products comprising machine-readable storage media for carrying or having machine-executable instructions or data structures stored thereon. Such machine-readable storage media can be any available media which can be accessed by a machine with a processor. By way of example, such machine-readable storage media can include RAM, ROM, EPROM, EEPROM, flash memory or any other medium which can be used to carry or store desired program code in the form of machine-executable instructions or data structures and which can be accessed by a machine with a processor. Combinations of the above are also included within the scope of machine-readable storage media. Machine-executable instructions include, for example, instructions and data which cause a processing machine to perform a certain function or group of functions. Machine or computer-readable storage media, as referenced herein, do not include transitory media (i.e., signals in space).

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

It should be noted that although the flowcharts provided herein show a specific order of method steps, it is understood that the order of these steps may differ from what is depicted. Also, two or more steps may be performed concurrently or with partial concurrence. Such variation will depend on the software and hardware systems chosen and on designer choice. All such variations are within the scope of the disclosure. It should be noted as well that the word "component," as used herein and in the claims, is intended to encompass implementations using one or more lines of software code and/or hardware implementations and/or equipment for receiving manual inputs.

The foregoing disclosure of embodiments has been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described to explain the principles of the disclosure and its practical application, to enable one skilled in the art to utilize the disclosure in various embodiments and with various modifications as are suited to the particular use contemplated.

What is claimed is:

1. A device configured for implantation in a vasculature of a heart of a patient for electrical stimulation of at least one of a first chamber and a second chamber of the heart, the device comprising:
   a flexible, elongated body that has a first end and an opposite second end, wherein the body has a tubular shape across a length of the body between the first end and the opposite second end;
   a first set of one of more electrodes at the first end configured for placement in a first section of the vasculature to electrically stimulate the first chamber of the heart;
   a second set of one of more electrodes at the second end configured for placement in a second section of the vasculature to electrically stimulate the second chamber of the heart; and
   a receiver circuit configured to receive signals wirelessly from a transmitter device and to convert the signals into electrical power, wherein the electrical power is used to provide electrical stimulation to the first chamber via the first set of electrodes and the second chamber via the second set of electrodes.

2. The device according to claim 1, wherein the receiver circuit is configured to receive the signals wirelessly from the transmitter device, to convert the signals into electrical power, and to transmit the electrical power directly to the first set of one or more electrodes and the second set of one or more electrodes to stimulate the heart.

3. The device according to claim 1, further comprising (a) an energy storage device configured to receive and to store the electrical power from the receiver circuit and (b) a stimulation circuit configured to transmit stimulation signals to the first set of one or more electrodes and the second set of one or more electrodes using the electrical power stored in the energy storage device.

4. The device according to claim 3, wherein the signals received from the transmitter comprise control signals configured to control one or more parameters of the stimulation signals transmitted to the first set of one or more electrodes and the second set of one or more electrodes by the stimulation circuit.

5. The device according to claim 3, wherein the stimulation circuit comprises a stimulation control circuit configured to control the provision of stimulation to the heart by the first set of one or more electrodes and the second set of one or more electrodes without requiring external control signals to be received from the transmitter device.

6. The device according to claim 1, wherein the first set of one or more electrodes is positioned within the first section of the vasculature and the second set of one or more electrodes is positioned within the second section of the vasculature, wherein at least one of the first section and the second section of the vasculature into which the body is configured to be positioned is external to the heart, and wherein at least one of the first set of one or more electrodes and the second set of one or more electrodes is configured to epicardially stimulate at least one of the first chamber and the second chamber of the heart.

7. The device according to claim 6, wherein the first section of the vasculature comprises a coronary vein and the second section of the vasculature comprises a coronary sinus, wherein the first set of one or more electrodes is configured to epicardially stimulate a left ventricle of the heart, and wherein the second set of one or more electrodes is configured to epicardially stimulate a left atrium of the heart.

8. The device according to claim 1, wherein the first and second ends are open ends and wherein the body has a central lumen that communicates with both ends.

9. The device according to claim 1, wherein the first and second ends are closed ends.

10. The device according to claim 1, wherein the receiver circuit comprises a plurality of coils distributed across the length of the body.

11. The device according to claim 1, wherein the receiver circuit is configured to receive the signals from the transmitter device using one or more of inductive coupling, radio frequency radiation, and ultrasound radiation.

12. The device according to claim 11, wherein the receiver circuit is configured to receive power signals from the transmitter device using one of inductive coupling, radio frequency radiation, and ultrasound radiation, and wherein the receiver circuit is configured to receive control signals configured to control one or more parameters of stimulation provided to the heart using another of inductive coupling, radio frequency radiation, and ultrasound radiation.

13. The device according to claim 1, wherein at least one of the first end and the second end of the body comprises a deployment attachment configured to allow a deployment device to disengage and reengage from the body within the vasculature without requiring removal of the deployment device and body from the patient.

14. The device according to claim 1, wherein at least one of the first end and the second end of the body comprises an anchoring attachment configured to stabilize at least a portion of the device in a substantially immobile position after the device has been inserted in the vasculature.

15. The device according to claim 14, wherein the anchoring attachment and at least one of the one or more electrodes together comprise an active stent.

16. The device according to claim 1, wherein the device is configured for use during a magnetic resonance imaging (MRI) procedure.

17. The device according to claim 1, further comprising an energy harvesting circuit configured to generate electrical energy to be used in stimulating the heart from flexural motion generated during a cardiac cycle.

* * * * *